United States Patent [19]

Stecher et al.

[11] 4,229,414

[45] Oct. 21, 1980

[54] ADHERENCE COLUMN

[75] Inventors: Vera J. Stecher; George L. Chinea, both of Dobbs Ferry, N.Y.

[73] Assignee: Ciba-Geigy Corporation, Ardsley, N.Y.

[21] Appl. No.: 33,790

[22] Filed: Apr. 27, 1979

[51] Int. Cl.$^2$ .................... G01N 31/06; G01N 33/16; G01N 21/24

[52] U.S. Cl. ................................ 422/101; 23/230 B; 422/59; 422/100

[58] Field of Search ............... 23/230 B; 422/101, 100

[56] References Cited

U.S. PATENT DOCUMENTS 3,999,944  12/1976  Grosser .............................. 424/12 X

OTHER PUBLICATIONS

R. R. MacGregor et al., N. Engl. J. Med., 642(13), 642–646 (1974).
Sargent–Welch Sci. Co. Catalog, p. 156, 1971.
Federation Proceedings, 35, No. 3, abstract 1793 (1976).
Federation Proceedings, 36, No. 3, abstract 4209 (1977).

Primary Examiner—Sidney Marantz
Attorney, Agent, or Firm—Harry Falber

[57] ABSTRACT

A column for determining neutrophil adhesiveness in the study of the activity of anti-inflammatory agents which comprises a column with bottom closure and delivery means and packed with scrubbed nylon fiber to a density of about 200—350 g/l immediately adjacent said closure means.

3 Claims, 1 Drawing Figure

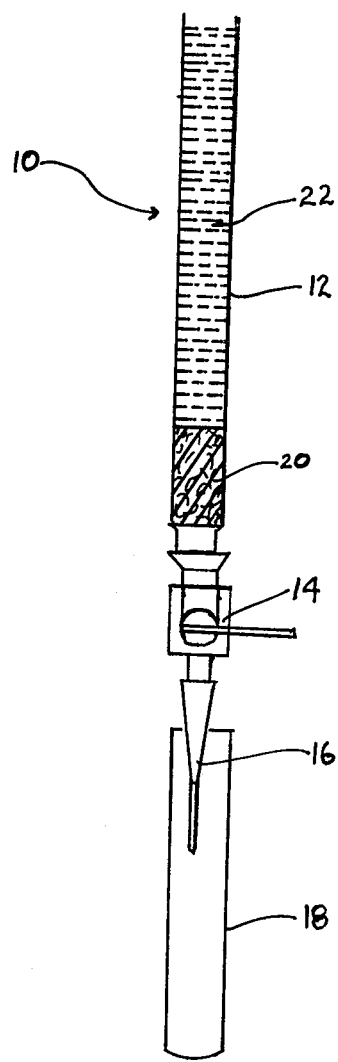

ADHERENCE COLUMN

Neutrophil adhesiveness is an important component of the pathophysiology of the inflammatory process. Modulation of this function could result in a reduction in the degree of inflammation and connective tissue damage. Gold and chloroquine, in addition to many standard anti-inflammatory drugs, have been shown to cause inhibition of neutrophil adherence. Measurement of this parameter of cell behavior has the potential of detecting anti-inflammatory agents not normally effective in the standard animal models.

During the inflammatory response, circulating neutrophils adhere to the venular endothelium and migrate into the tissue. There is little doubt that the accumulation of neutrophils is an important component in the pathogenesis of rheumatoid arthritis. It has been noted, for example, that in the rheumatoid joint the accumulation of 500 million leukocytes per 10 ml effusion is a characteristic of this inflammatory response. Modulation of neutrophil adherence therefore might be a realistic therapeutic goal that could result in a reduction in the degree of inflammation.

Accordingly, there is a need for an assay that will detect not only "classic" nonsteroidal anti-inflammatory drugs, but gold and chloroquine-like compounds as well. It has been shown by MacGregor et al. [New Engl. J. Med. 291, 642–646 (1974)] that peripheral blood granulocytes from human volunteers who received prednisone or aspirin had a reduced ability to adhere to nylon fiber columns packed in Pasteur pipettes. The technique of MacGregor requires however, that the Pasteur pipette tips be heated and drawn out to a critical length and tip opening. Likewise, a method reported by Garvin [J. Exp. Med. 114, 51–73 (1961)] for studying adhesiveness of human leukocytes has required an elaborate column attached to a motor-driven syringe. Neither of these approaches has provided a rapid, simple and reproducible method for determining the adhesiveness of peripheral blood neutrophils from rats treated with anti-inflammatory agents. A further approach has been suggested by Lorente et al., Journal of Inmunological Methods 19, 47–51 (1978). This procedure utilizes a column of glass beads in order to measure granulocyte adherence.

It is, accordingly, the primary object of this invention to provide an adherence column for determining neutrophil adhesiveness in a rapid, simple and reproducible manner.

It is a further object to provide such a column which will facilitate detection of gold and chloroquine-like compounds in addition to standard anti-inflammatory agents.

It is another to provide a technique for detecting anti-inflammatory agents not normally effective in standard animal models.

It is still another object to provide such a system which is readily adaptable to a large screening program.

Various other objects and embodiments of this invention will become apparent from the discussion that follows hereinafter.

We have now discovered that the above noted objectives can be achieved by means of a simple technique utilizing filtration of whole blood through a scrubbed nylon fiber plug compacted into a column. This technique and column arrangement provide a rapid, simple and readily reproducible method for the measurement of cell adherence, thereby facilitating the study of the behavioral potential of leukocytes following drug treatment of the whole animal or patient. As contrasted with the prior art approaches, it does not require elaborate instrumentation nor tedious and time-consuming processing of the glassware nor involved incubation procedures. The instant technique and apparatus also have the potential for use in the detection of various disease states as well as in general screening operations. They can also be useful as a means of detecting differences in the mechanism of action of drugs showing varying degrees of efficacy in this condition. It is proposed that this neutrophil adherence assay can be of value in detecting potential antirheumatic agents not readily picked up in the more routine tests. Finally, the test singles out the effect of drugs on one parameter which may be of basic importance in the etiology of rheumatoid arthritis.

To the accomplishment of the above, and to such other objects as may hereinafter appear, the present invention relates to the construction of an adherence column as defined in the appended claims and as described in this specification taken together with the accompanying drawing which is a front plan view of the instant adherence column.

More specifically, adherence column 10 consists of elongated column 12, closure means 14 and delivery means 16. The closure means 14 and delivery means 16 are positioned at the bottom end of column 12. Closure means 14 may comprise any element such as a stopcock which, in one position, can completely close the passage of fluid through column 12 while in a second position allows for the passage of fluid into delivery means 16. The latter can comprise any open passage, although a needle is preferred for directing the fluid into any collecting vessel 18.

The scrubbed nylon fiber 20 is compacted into column 12 approximately adjacent to closure means 14. Such fiber is commercially available, e.g. as prepared and sold by Fenwall Laboratories, Morton Grove, Ill. In order to obtain appropriate adherence, the nylon fiber 20 is compacted in a density ranging from about 200–350 g/l. Preferred variables are 80 mg of fiber compacted in a volume of 0.25 ml.

As an alternate to the column noted in the drawing, it is also possible to utilize a syringe or other similar columnar assembly. It is preferred for purposes solely of convenience that the column or syringe have a total volume of one ml.

The procedure for utilizing said column involves taking the whole blood sample 22 and introducing it into a closed, packed column which has been pre-incubated at a temperature of about 37° C. for a period of about 10 minutes. The filled column is then further incubated at the above temperature for an additional five minutes. The closing means is then opened and the blood sample is allowed to filter through the packed nylon by means of gravitational force for a period of about 15 minutes which is sufficient to have complete drainage of the sample. Total blood leukocyte counts are then made on the refrigerated, filtered sample by appropriate instrumentation such as a Coulter Counter. The percent of neutrophils is then multiplied by the total white blood cell counts to determine the total number of neutrophils/mm$^3$. These values are compared with comparable values of unfiltered blood in order to obtain percent inhibition of adherence.

The following examples will further illustrate the embodiment of this invention.

EXAMPLE I

This example illustrates a typical column of the instant invention and its use in determining adherence values.

The adherence column used in these studies consisted of a one ml disposable tuberculin syringe packed to the 0.25 ml mark with 80 mg scrubbed nylon fiber and fitted with a stopcock and 25 gauge ⅝ inch disposable needle.

The procedure involved taking heparinized blood (preservative-free heparin) from the abdominal aorta of each treated rat and placing it on the adherence column. Five animals were used in each treatment group. The packed columns were pre-incubated at 37° C. for 10 minutes. After this period of warming, 1 ml of blood was placed on the columns using a tuberculin syringe fitted with a 14 G, 4-inch needle and incubated for five minutes at 37° C. The stopcocks were opened and the blood allowed to filter through the scrubbed nylon fiber by gravitational force for an additional 5 minutes. A control aliquot of unfiltered blood was incubated in comparable tubes for the same length of time. Following the incubation time, and prior to counting, the blood samples were kept on ice. Total blood leukocyte counts were determined with the Coulter Counter, Model ZBI, and differential counts (200 cells/slide, 2 slides/sample) were taken on the filtered blood and unfiltered control blood. The percent of neutrophils were multiplied by the total white blood cell counts to determine the total number of neutrophilis/mm$^3$. The values obtained for blood filtered through the nylon fiber column were subtracted from those values of the unfiltered blood for each animal. The percent of neutrophils retained on the adherence columns in the treated group was compared with that of the untreated control group and percent inhibition of adherence was calculated.

All the drugs except gold listed in the following table were given orally for five days; the final dose being given one hour prior to the test. The drugs were homogenized in an aqueous vehicle consisting of 3% cornstarch, 5% polyethylene glycol 400 and 2 drops of surfactant. The untreated control groups received vehicle alone. Male rats, weighing 225 to 235 g, were used exclusively in this study. Gold, sodium thiomalate, Myochrysine, was administered by intra-muscular injection (25 mg/kg). The inhibition values are determined in comparison with non-treated control animals.

| Drug | Dose (mg/kg) | #of Expts. | % Inhibition of Neutrophil Adherence |
|---|---|---|---|
| Indomethacin | 2 | 3 | 54 |
| Colchicine | 2 | 2 | 66 |
| Aspirin | 100 | 3 | 53 |
| Phenylbutazone | 100 | 2 | 54 |
| Gold | 25 | 4 | 43 |
| Mefanimic Acid | 100 | 1 | 45 |
| Chloroquine | 25 | 3 | 37 |
| Paramethasone | 0.5 | 1 | 34 |
| DL-Penicillamine | 100 | 2 | 54 |
| Ibuprofen | 100 | 1 | 38 |

While the standard anti-inflammatory drugs are picked up by this assay as anticipated, the data shows quite clearly that in addition both gold (i.m. 25 mg/kg) and chloroquine (p.o. 25 mg/kg) are detected. The adherence assay, performed as described, has provided a method for detecting the activity of various types of anti-inflammatory compounds.

EXAMPLE II

The procedure and column of Example I was used to illustrate that there is a dose response relationship in the effect of aspirin on neutrophil adherence. The higher the dose, the lower the number of neutrophils which adhered to the nylon fiber. At 25 mg/kg p.o. the percent of neutrophils adhering approached control values. The dose-response pattern seen with aspirin appears to be typical of that obtained with other anti-inflammatory compounds.

The data, as determined by the procedure of Example I, is presented in the following table:

| Treatment | Dose (mg/kg p.o.) | % of Neutrophils Adhering |
|---|---|---|
| 3% Cornstarch | 1 ml/100 gbw | 77.9 ± 2.7 |
| Aspirin | 100 | 57.1 ± 3.9 |
| Aspirin | 50 | 65.9 ± 3.4 |
| Aspirin | 25 | 73.2 ± 4.4 |

Summarizing, it is seen that the present invention provides a novel column arrangement and procedure for determining cell adherence of a virtually unlimited number of drugs. Variations may be made in procedures and materials without departing from the scope of the invention as defined by the following claims.

We claim:

1. An assembly for determining neutrophil adherence comprising a column, closure and delivery means positioned at the bottom end thereof and nylon fibers packed into said column approximately adjacent said closure means, said fibers being packed in said column in a density of from about 200-350 g/l.

2. The assembly of claim 1, wherein 80 mg. of said fibers were packed into said column in a volume of 0.25 ml.

3. The assembly of claim 1, wherein said column is a 1 ml. syringe.